(12) United States Patent

Zhang et al.

(10) Patent No.: US 12,611,221 B2

(45) Date of Patent: Apr. 28, 2026

(54) SCALPEL ROD ASSEMBLY OF ULTRASONIC SCALPEL

(71) Applicant: SHANGHAI SHENGZHE MEDICAL TECHNOLOGY CO., LTD., Shanghai (CN)

(72) Inventors: Wenliang Zhang, Shanghai (CN); Xianglu Wu, Shanghai (CN); Jizhen Ma, Shanghai (CN); Qian Chen, Shanghai (CN); Jianjiao Yu, Shanghai (CN)

(73) Assignee: Shanghai Shengzhe Medical Technology Co., Ltd., Shanghai (CN)

( * ) Notice: Subject to any disclaimer, the term of this patent is extended or adjusted under 35 U.S.C. 154(b) by 332 days.

(21) Appl. No.: 18/273,840

(22) PCT Filed: Aug. 18, 2021

(86) PCT No.: PCT/CN2021/113150

§ 371 (c)(1), (2) Date: Jul. 22, 2024

(87) PCT Pub. No.: WO2022/134625

PCT Pub. Date: Jun. 30, 2022

(65) Prior Publication Data

US 2025/0176990 A1 Jun. 5, 2025

(30) Foreign Application Priority Data

Dec. 21, 2020 (CN) .......................... 202011519135.0

(51) Int. Cl.
| | |
|---|---|
| *A61B 17/32* | (2006.01) |
| *A61B 17/00* | (2006.01) |
| *A61B 90/00* | (2016.01) |

(52) U.S. Cl.
CPC ...... *A61B 17/320068* (2013.01); *A61B 90/03* (2016.02); *A61B 2017/00477* (2013.01); (Continued)

(58) Field of Classification Search
CPC ............ A61B 17/320068; A61B 90/03; A61B 2090/034; A61B 2017/320074; (Continued)

(56) References Cited

U.S. PATENT DOCUMENTS 5,346,502 A * 9/1994 Estabrook ...... A61B 17/320068
76/119
5,935,144 A 8/1999 Estabrook
(Continued)

FOREIGN PATENT DOCUMENTS

| CN | 104783868 A | 7/2015 |
|---|---|---|
| CN | 108354652 A | 8/2018 |

(Continued)

OTHER PUBLICATIONS

Search Report issued to European counterpart Application No. 21908630.3 dated Sep. 23, 2024.

(Continued)

*Primary Examiner* — Ashley L Fishback

(74) *Attorney, Agent, or Firm* — McNees Wallace & Nurick

(57) ABSTRACT

Example embodiments disclose a scalpel rod assembly of an ultrasonic scalpel. The scalpel rod assembly includes a scalpel rod, an inner tube, and a support ring; the inner tube is sleeved outside the scalpel rod; the support ring includes a first support body, the first support body is provided on the inner wall of the inner tube, and a first protrusion protrudes from the first support body in a direction away from the inner tube until the first protrusion abuts against the scalpel rod.

10 Claims, 5 Drawing Sheets

(52) U.S. Cl.
CPC .............. *A61B 2017/00836* (2013.01); *A61B 2017/00862* (2013.01); *A61B 2017/00938* (2013.01); *A61B 2017/00946* (2013.01); *A61B 2017/320074* (2017.08); *A61B 2090/034* (2016.02)

(58) Field of Classification Search
CPC ........... A61B 2017/00477; A61B 2017/00836; A61B 2017/00862; A61B 2017/00938; A61B 2017/00946
See application file for complete search history.

(56) References Cited

U.S. PATENT DOCUMENTS

| | | | | |
|---|---|---|---|---|
| 6,176,703 | B1 | 1/2001 | Gugel et al. | |
| 2002/0138090 | A1 | 9/2002 | Jewett | |
| 2017/0172700 | A1* | 6/2017 | Denzinger | ..... A61B 17/320068 |

FOREIGN PATENT DOCUMENTS

| | | | | |
|---|---|---|---|---|
| CN | 209808382 | U | 12/2019 | |
| CN | 210095855 | U | 2/2020 | |
| CN | 111658079 | A * | 9/2020 | ..... A61B 17/320092 |
| CN | 211560271 | U | 9/2020 | |
| CN | 211561628 | U | 9/2020 | |
| CN | 112472224 | A | 3/2021 | |
| CN | 116327322 | B * | 1/2024 | ..... A61B 17/320068 |
| WO | 9837819 | A1 | 9/1998 | |

OTHER PUBLICATIONS

International Search Report issued to counterpart Applciation No. PCT/CN2021/113150 dated Nov. 2, 2021.
First Office Action for counterpart Application No. CN202011519135.0 dated May 7, 2021.
Second Office Action for counterpart Application No. CN202011519135.0 dated Jul. 16, 2021.

* cited by examiner

SCALPEL ROD ASSEMBLY OF ULTRASONIC SCALPEL

CROSS-REFERENCE TO RELATED APPLICATIONS

This is a National Stage Application, filed under 35 U.S.C. 371, of International Patent Application No. PCT/CN2021/113150, filed on Aug. 18, 2021, which claims priority to Chinese patent application No. 202011519135.0 filed on Dec. 21, 2020, contents of both of which are incorporated herein by reference in their entireties.

TECHNICAL FIELD

The present application relates to the field of medical instruments, for example, to a scalpel rod assembly of an ultrasonic scalpel.

BACKGROUND

The ultrasonic scalpel has been widely used in clinical surgery due to the advantages of low bleeding, little damage to surrounding tissues, etc. The conventional scalpel rod assembly of the ultrasonic scalpel supports the scalpel rod inside the outer sleeve by means of a support ring provided on the scalpel rod. The support ring is attached to the inner wall of the outer sleeve, and the impedance of the scalpel rod is easily increased so that the scalpel rod may be easily heated up during the working process, affecting the normal use of the scalpel rod assembly. The support ring is integrally molded on the scalpel rod by injection molding, glue is easily spilled during the processing, and the surface of the scalpel rod may be easily scratched in the process of cleaning the spilled glue, resulting in the change in the vibration frequency of the scalpel rod.

SUMMARY

The present application provides a scalpel rod assembly of an ultrasonic scalpel to solve the problems of increased impedance and spilled glue caused by the support ring provided on the scalpel rod.

The present application provides a scalpel rod assembly of an ultrasonic scalpel. The scalpel rod assembly includes a scalpel rod, an inner tube, and a support ring. The inner tube is sleeved outside the scalpel rod. The support ring includes a first support body. The first support body is provided on the inner wall of the inner tube, and a first protrusion protrudes from the first support body in a direction away from the inner tube until the first protrusion abuts against the scalpel rod.

As an optional solution of the scalpel rod assembly, the support ring further includes a second support body and a connector. The second support body is provided on the outer wall of the inner tube. A through hole is provided on the inner tube, the connector is provided inside the through hole, and the connector is connected to the first support body and the second support body.

As an optional solution of the scalpel rod assembly, the first support body, the connector and the second support body are an integrated structure.

As an optional solution of the scalpel rod assembly, multiple through holes are provided, and the multiple through holes are evenly distributed along the circumferential direction of the inner tube.

As an optional solution of the scalpel rod assembly, the support ring is integrally molded on the inner tube by injection molding.

As an optional solution of the scalpel rod assembly, the material of the support ring is silicone rubber.

As an optional solution of the scalpel rod assembly, the scalpel rod assembly includes an outer tube. The outer tube is sleeved outside the inner tube, and the second support body is clearance fitted with the outer tube.

As an optional solution of the scalpel rod assembly, the first protrusion is an annular protrusion.

As an optional solution of the scalpel rod assembly, two support rings are provided. The two support rings are a first support ring and a second support ring, respectively. The first support ring is provided at a head end of the inner tube, and the second support ring is provided at a tail end of the inner tube.

As an optional solution of the scalpel rod assembly, at least one of the first support ring or the second support ring is provided with a second protrusion that is annular. The second protrusion is provided on the outer wall of the second support body of at least one of the first support ring or the second support ring and extends in a direction away from the inner tube until the second protrusion abuts against an inner wall of the outer tube.

As an optional solution of the scalpel rod assembly, the scalpel rod, the inner tube and the support ring are provided coaxially.

REFERENCE NUMERALS

Figure 1:
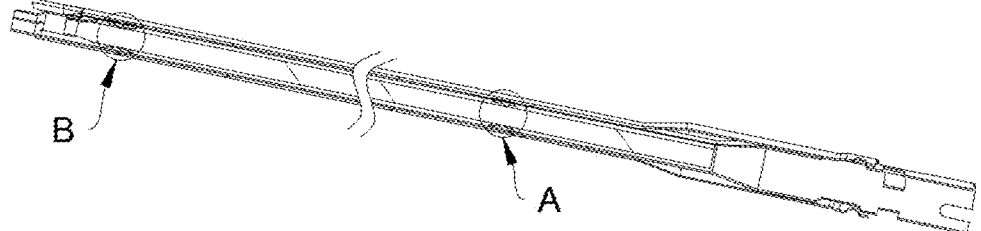
FIG. 1 is a section view of a scalpel rod assembly according to an embodiment of the present application.

1 scalpel rod
2 inner tube
3 support ring
4 outer tube
21 through hole
31 first support ring
311 first support body
3111 first protrusion
312 second support body
3121 second protrusion
313 connector
32 second support ring

DETAILED DESCRIPTION

Solutions in the embodiments of the present application will be described in conjunction with drawings in the embodiments of the present application. The embodiments described herein are part, not all, of the embodiments of the present application. The components of the embodiments of the present application, as generally described and illustrated in the drawings herein, may be arranged and designed in a wide variety of different configurations.

The following description of the embodiments of the present application, as presented in the drawings, is not intended to limit the scope of the present application, but is merely representative of selected embodiments of the present application.

Similar numerals and letters indicate similar items in the following drawings, and therefore, once a particular reference numeral or letter is defined in one drawing, the similar reference numeral or letter does not need to be defined and explained in the subsequent drawings.

In the description of the present application, the orientations or position relationships indicated by terms "above", "below", "left", "right", "vertical", "horizontal", "inside", and "outside" are based on the orientations or position relationships illustrated in the drawings or are the orientations or position relationships where the products of the present application are customarily placed for use. These orientations or position relationships are intended to facilitate and simplify the description of the present application and not to indicate or imply that a tool table or element referred to must have such specific orientations or must be configured or operated in such specific orientations. Thus, these orientations or position relationships are not to be construed as limiting the present application. Terms "first", "second" and "third" are merely for distinguishing the description and are not to be construed as indicating or implying relative importance. In the description of the present application, unless otherwise noted, the term "a plurality of" or "multiple" means two or more.

In the description of the present application, unless otherwise expressly specified and limited, the term "provided" or "connected" is to be construed in a broad sense, for example, as securely connected, detachably connected or integrated; or mechanically connected or electrically connected. For those of ordinary skill in the art, meanings of the preceding terms in the present application can be understood according to situations.

In the present application, unless otherwise expressly specified and limited, when a first feature is described as "on" or "below" a second feature, the first feature and the second feature may be in direct contact or be in contact via another feature between the two features such that the first and second features may not be in direct contact. When the first feature is described as "on", "above" or "over" the second feature, the first feature is right on, above or over the second feature, the first feature is obliquely on, above or over the second feature, or the first feature is simply at a higher level than the second feature. When the first feature is described as "under", "below" or "underneath" the second feature, the first feature is right under, below or underneath the second feature, the first feature is obliquely under, below or underneath the second feature, or the first feature is simply at a lower level than the second feature.

Embodiments of the present application are described below. Examples of the embodiments are illustrated in the drawings, where the same or similar reference numerals indicate the same or similar elements or elements having the same or similar functions. The embodiments described below with reference to the drawings are illustrative, are intended to explain the present application, and cannot be construed as limiting the present application.

As shown in FIGS. 1 to 7, the present application provides a scalpel rod assembly of an ultrasonic scalpel. The scalpel rod assembly includes a scalpel rod 1, an inner tube 2, and a support ring 3. The inner tube 2 is sleeved outside the scalpel rod 1. The support ring 3 includes a first support body 311. The first support body 311 is provided on the inner wall of the inner tube 2, a first protrusion 3111 protrudes from the first support body 311 in a direction away from the inner tube 2, and the first protrusion 3111 abuts against the scalpel rod 1, thereby supporting the scalpel rod 1 inside the inner tube 2.

In the present embodiment, the support ring 3 is provided on the inner tube 2 and the first protrusion 3111 protrudes on the support ring 3 to support the scalpel rod 1 and avoid large-area contact between the support ring 3 and the scalpel rod 1. In this manner, the impedance of the scalpel rod 1 is reduced, the loss of the scalpel rod assembly during the process of energy conversion is reduced, and the situation that the scalpel rod 1 is overheated to affect normal use is avoided; moreover, the situation that the surface of the scalper rod 1 is worn due to the cleaning of spilled glue to result in the change in the working frequency of the scalper rod 1 is avoided.

Figure 2:
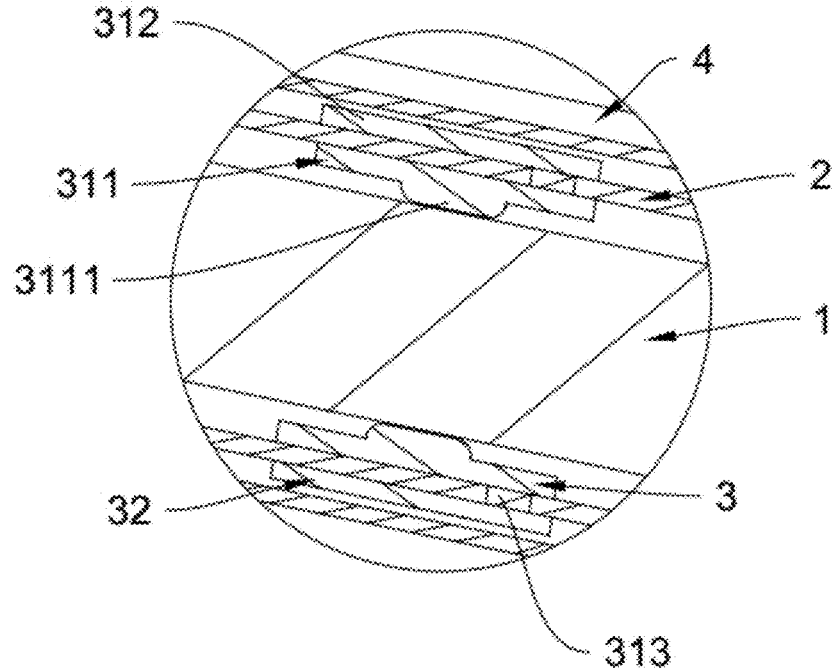
FIG. 2 is a partial enlarged view of part A in FIG. 1.
Figure 3:
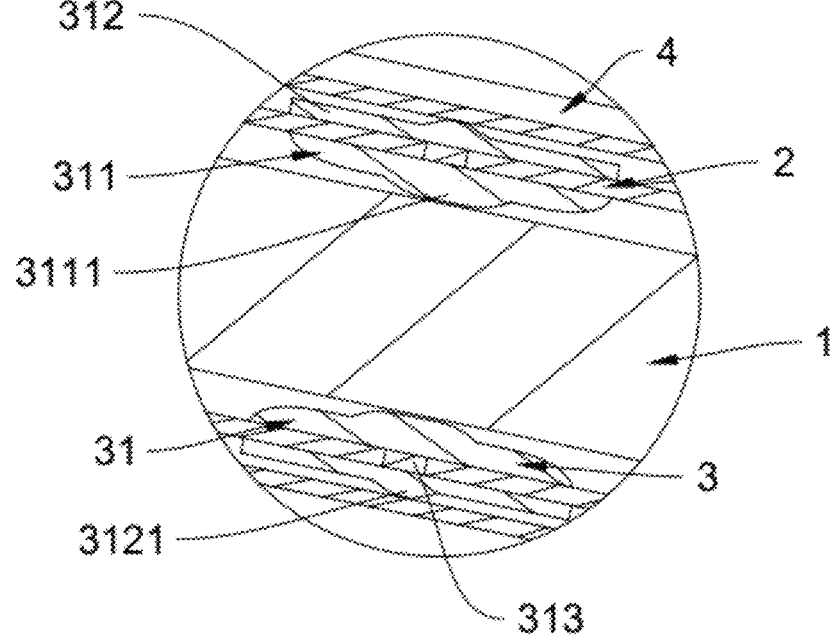
FIG. 3 is a partial enlarged view of part B in FIG. 1.
Figure 4:
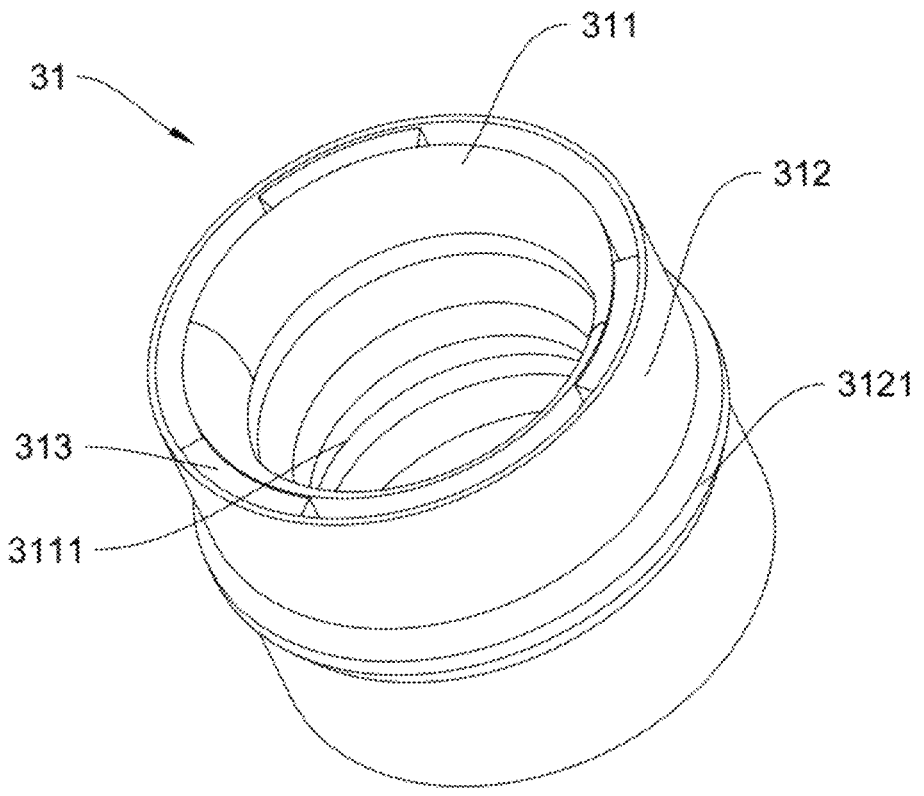
FIG. 4 is a structure view of a first support ring according to an embodiment of the present application.
Figure 5:
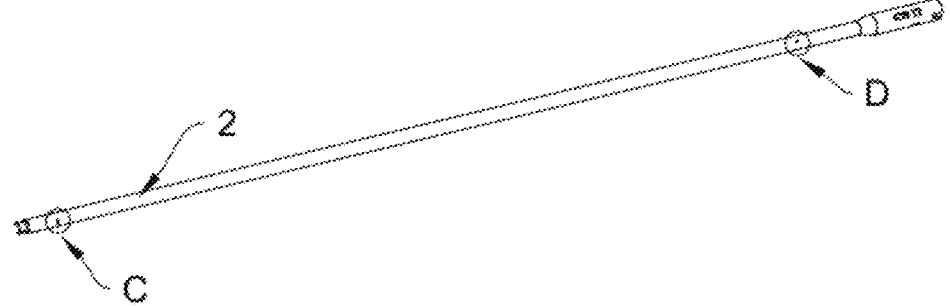
FIG. 5 is a structure view of an inner tube according to an embodiment of the present application.
Figure 6:
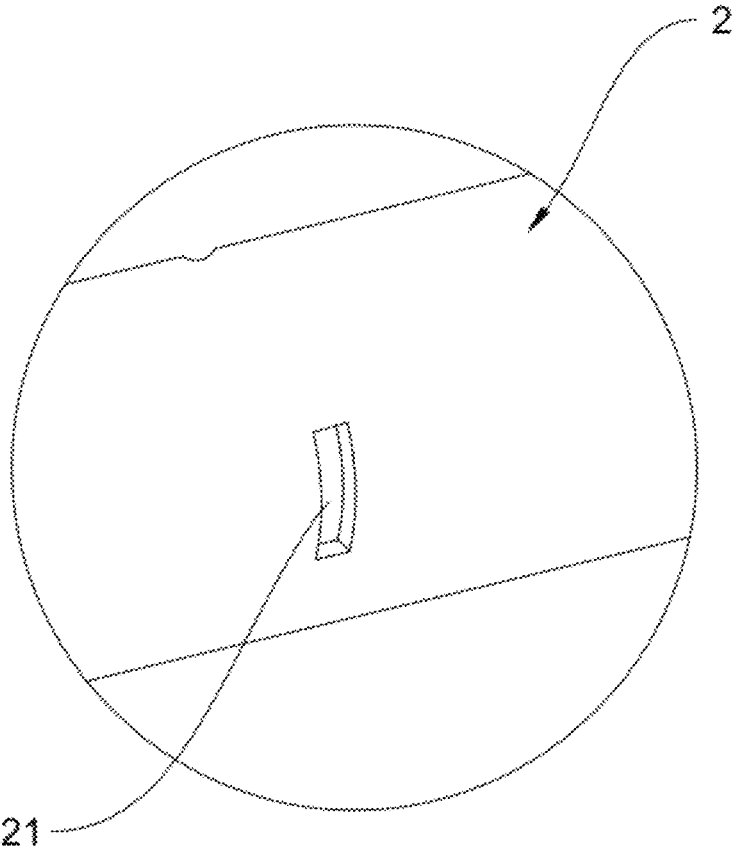
FIG. 6 is a partial enlarged view of part C in FIG. 5.
Figure 7:
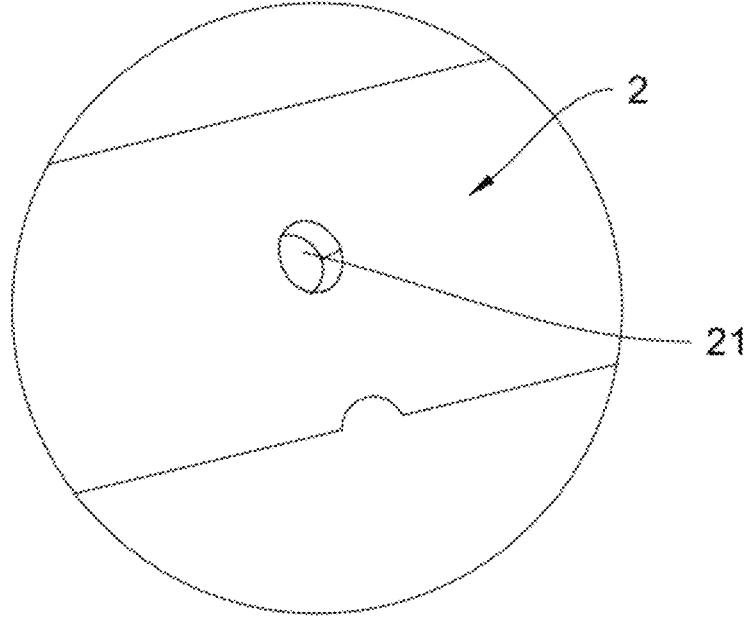
FIG. 7 is a partial enlarged view of part D in FIG. 5.

In conjunction with FIGS. 2 to 4, in the present application, the support ring 3 further includes a second support body 312 and a connector 313. The second support body 312 is provided on the outer wall of the inner tube 2. A through hole 21 is provided on the inner tube 2, the connector 313 is provided inside the through hole 21, and the connector 313 is connected to the first support body 311 and the second support body 312. The design of the connector 313 in the through hole 21 enables the positioning of the support ring 3 on the inner tube 2, and the design of the second support body 312 increases the attachment of the support ring 3 as a whole to the inner tube 2 so that the support ring 3 is less easily disengaged from the inner tube 2. Optionally, the first support body 311, the connector 313 and the second support body 312 are an integrated structure, avoiding the situation that the reliability of the support ring 3 is reduced due to the assembly dislocation of the first support body 311 and the second support body 312 when the combined structure is adopted. Optionally, the support ring 3 is integrally molded on the inner tube 2 by injection molding, not only facilitating the assembly of the support ring 3 and the inner tube 2 but also improving the integrity of the support ring 3 and the inner tube 2. At this point, the through hole 21 becomes a flow channel of a molten material. Optionally, an adhesive coating is provided on the contact surface of the support ring 3 and the inner tube 2, enhancing the attachment of the support ring 3 to the inner tube 2. Optionally, multiple through holes 21 are provided, and the multiple through holes 21 are evenly distributed along the circumferential direction of the inner tube 2. The molten material can be simultaneously injected into the multiple through holes 21, saving the processing time of the support ring 3 on the inner tube 2 and improving the injection molding efficiency of the support ring 3. Optionally, the material of the support ring is silicone rubber which can provide better adhesion and seismic resistance, improving fatigue resistance and aging resistance of the support ring. As shown in FIGS. 5 to 7, in the present application, two support rings 3 are provided. The two support rings are a first support ring 31 and a second support ring 32, respectively. Three strip through holes are provided on the contact surface of the first support ring 31 and the inner tube 2, and four cylindrical through holes are provided on the contact surface of the second support ring 32 and the inner tube 2. The injection molding efficiency of the support ring 3 is related to the number and the cross-sectional area of the through holes 21. The larger the number and the cross-sectional area of the through holes 21 are, the higher the injection molding efficiency of the support ring 3 is.

As shown in FIG. 4, optionally, the first protrusion 3111 is an annular protrusion to achieve the sealing connection between the inner tube 2 and the scalper rod 1, avoiding backflow of blood between the inner tube 2 and the scalper rod 1 when the scalper rod assembly works. As shown in FIGS. 2 to 3, optionally, the scalpel rod assembly further includes an outer tube. The outer tube 4 is sleeved outside the inner tube 2, and the second support body 312 is clearance fitted with the outer tube 4 to leave sufficient space for the scalpel rod 1 to be inserted into the inner tube 2. The support ring 3 is molded on the inner tube 2 by injection molding, the outer tube 4 is sleeved on the inner tube 2, and finally, the scalpel rod 1 is inserted into the inner tube 2 to achieve assembly of the scalpel rod assembly. During the assembly, since the first protrusion 3111 enables the scalpel rod 1 to compress the support ring 3 towards the outer tube 4, the clearance fit of the second support body 312 and the outer tube 4 can leave space for the scalpel rod 1 to insert, facilitating the assembly of the scalpel rod 1. After the scalpel rod 1 is assembled in place, the first protrusion 3111 on the support ring 3 forms the sealing connection with the scalpel rod 1 to allow the support ring 3 to support the scalpel rod 1 and to achieve the sealing between the scalpel rod 1 and the inner tube 2. Optionally, two support rings 3 are provided. The two support rings are a first support ring 31 and a second support ring 31, respectively. The first support ring 31 is provided at a head end of the inner tube 2, and the second support ring 32 is provided at a tail end of the inner tube 2. The first support ring 31 and the second support ring 32 guide the assembly of the scalpel rod 1. Optionally, at least one of the first support ring 31 or the second support ring 32 is provided with a second protrusion 3121 that is annular. The second protrusion 3121 is provided on the outer wall of the second support body 312 of at least one of the first support ring 31 or the second support ring 32 and extends in a direction away from the inner tube 2 until the second protrusion 3121 abuts against the inner wall of the outer tube 4 to achieve sealing between the inner tube 2 and the outer tube 4. The sealing between the inner tube 2 and the outer tube 4 allows a closed space to be formed between the scalpel rod assembly and the body of a patient to avoid leakage of drug gas, and further avoids the backflow of the blood of the of a patient during surgery. In the present embodiment, the second protrusion 3121 is provided on the second support body 312 of the first support ring 31, and the second support body 312 of the second support ring 32 is clearance fitted with the outer tube 4, facilitating the insert of the scalpel rod 1 into the inner tube 2 and achieving the sealing between the scalpel rod 1 and the outer tube 4.

The scalpel rod 1, the inner tube 2 and the support ring 3 are provided coaxially to make the structure of the scalpel rod assembly reasonable. Optionally, the first protrusion 3111 is in line contact with the scalpel rod 1, further reducing the impedance of the scalpel rod 1.

What is claimed is:

1. A scalpel rod assembly of an ultrasonic scalpel, comprising:
   a scalpel rod;
   an inner tube, wherein the inner tube is sleeved outside the scalpel rod;
   a support ring, wherein the support ring comprises a first support body, the first support body is provided on an inner wall of the inner tube, and a first protrusion protruding from the first support body in a direction away from the inner tube, wherein the first protrusion abuts against the scalpel rod; and a second support body, wherein the second support body is provided on an outer wall of the inner tube; and a connector, wherein a through hole is provided on the inner tube, the connector is provided inside the through hole, and the connector is connected to the first support body and the second support body.

2. The scalpel rod assembly of claim 1, wherein the first support body, the connector and the second support body are an integrated structure.

3. The scalpel rod assembly of claim 2, wherein the support ring is integrally molded on the inner tube by injection molding.

4. The scalpel rod assembly of claim 2, wherein a material of the support ring is silicone rubber.

5. The scalpel rod assembly of claim 1, wherein a plurality of through holes are provided, and the plurality of through holes are evenly distributed along a circumferential direction of the inner tube.

6. The scalpel rod assembly of claim 1, further comprising an outer tube, wherein the outer tube is sleeved outside the inner tube, and the second support body is clearance fitted with the outer tube.

7. The scalpel rod assembly of claim 6, wherein two support rings are provided, the two support rings are a first support ring and a second support ring, respectively, the first support ring is provided at a head end of the inner tube, and the second support ring is provided at a tail end of the inner tube.

8. The scalpel rod assembly of claim 7, wherein at least one of the first support ring or the second support ring is provided with a second protrusion that is annular, and the second protrusion is provided on an outer wall of the second support body of the at least one of the first support ring or the second support ring and extends in a direction away from the inner tube until the second protrusion abuts against an inner wall of the outer tube.

9. The scalpel rod assembly of claim 1, wherein the first protrusion is an annular protrusion.

10. The scalpel rod assembly of claim 1, wherein the scalpel rod, the inner tube and the support ring are provided coaxially.

\* \* \* \* \*